US006521097B2

(12) United States Patent
Geissler

(10) Patent No.: US 6,521,097 B2
(45) Date of Patent: Feb. 18, 2003

(54) PROCESS FOR SEPARATING HYDROGEN CHLORIDE FROM A MIXTURE COMPRISING AN N-ALKYL-2-PYRROLIDONE AND HYDROGEN CHLORIDE

(75) Inventor: Holger Geissler, Mainz (DE)

(73) Assignee: Clariant GmbH, Frankfurt (DE)

( * ) Notice: Subject to any disclaimer, the term of this patent is extended or adjusted under 35 U.S.C. 154(b) by 23 days.

(21) Appl. No.: 09/892,595

(22) Filed: Jun. 27, 2001

(65) Prior Publication Data

US 2002/0014399 A1 Feb. 7, 2002

(30) Foreign Application Priority Data

Jun. 27, 2000 (DE) ......................... 100 31 288

(51) Int. Cl.[7] .................. B01D 3/38; C07D 207/26; C01B 7/07
(52) U.S. Cl. .................. 203/93; 203/94; 203/96; 203/97; 203/98; 423/488; 548/555
(58) Field of Search .................. 203/91–98, 100; 423/481, 488; 548/555

(56) References Cited

U.S. PATENT DOCUMENTS

| 3,399,119 | A | | 8/1968 | Hall et al. ..................... 203/38 |
| 3,640,851 | A | * | 2/1972 | Mourier ....................... 203/96 |
| 3,651,166 | A | | 3/1972 | Hall ............................ 423/481 |
| 3,658,659 | A | | 4/1972 | Cottle ......................... 203/69 |
| 4,057,491 | A | * | 11/1977 | Bushnell et al. .............. 203/82 |
| 4,276,126 | A | | 6/1981 | Saffer ......................... 203/69 |
| 6,075,152 | A | | 6/2000 | Geissler et al. ............. 549/290 |

FOREIGN PATENT DOCUMENTS

EP 0 949 256 10/1999

OTHER PUBLICATIONS

Derwent Abstract of EP 0 949 256.
EPO Search Report for EP Application No. 01114524, mail date Oct. 22, 2001.

* cited by examiner

Primary Examiner—Virginia Manoharan
(74) Attorney, Agent, or Firm—Scott E. Hanf

(57) ABSTRACT

A process for separating hydrogen chloride from a mixture including an N-($C_1$–$C_{18}$)-alkyl-2-pyrrolidone and hydrogen chloride by distilling the mixture including an N-($C_1$–$C_{18}$)-alkyl-2-pyrrolidone and hydrogen chloride at from 100 to 220° C. and from 50 to 850 hPa in the presence of water in a distillation column, condensing the water as water-hydrogen chloride azeotrope at the top by cooling, returning the water-hydrogen chloride azeotrope to the distillation column, separating off gaseous hydrogen chloride at the top and taking off the N-($C_1$–$C_{18}$)-alkyl-2-pyrrolidone from the bottom.

7 Claims, No Drawings

PROCESS FOR SEPARATING HYDROGEN CHLORIDE FROM A MIXTURE COMPRISING AN N-ALKYL-2-PYRROLIDONE AND HYDROGEN CHLORIDE

FIELD OF THE INVENTION

The present invention relates to a process for separating hydrogen chloride from a mixture comprising an N-alkyl-2-pyrrolidone and hydrogen chloride by means of distillation.

BACKGROUND OF THE INVENTION

N-Alkylpyrrolidone containing hydrogen chloride is formed in the preparation of isochroman-3-ones by the process described in EP 0 949 256. When N-methyl-2-pyrrolidone is used, an N-methyl-2-pyrrolidone containing hydrogen chloride is obtained. After hydrogen chloride has been separated off, the N-methyl-2-pyrrolidone can be reused in the process. The reuse of the N-methyl-2-pyrrolidone is advantageous both from an economic point of view and in terms of ecologocial aspects. Reuse avoids undesirable waste products which would have to be disposed of.

U.S. Pat. No. 3,651,166 concerns a process for recovering hydrogen halide and organic bases, for example N-methyl-2-pyrrolidone, by heating their salts to dissociation temperature. Example II describes the recovery of anhydrous HCl from an N-methyl-2-pyrrolidone (NMP) solution containing water and HCl by distillation. Here, the water is firstly distilled off until the temperature has reached about 120° C. Residual water and a small proportion of the NMP is then distilled off at 150° C. Anhydrous HCl is subsequently separated off at from 175 to 180° C.

Although anhydrous HCl is obtained in this way, this HCl is contaminated with N-methylpyrrolidone to a not inconsiderable extent and cannot be directly processed further. Rather, this contaminated HCl either has to be purified in a separate, costly process or has to be disposed of. Furthermore, entrained solids (sublimates) can deposit at the top of the distillation column and in the downstream lines and lead to blockages. See also Comparative Example 2A.

SUMMARY OF THE INVENTION

There is therefore a need for a process which avoids the abovementioned disadvantages, can be implemented in a simple manner, gives pure hydrogen chloride and makes possible a satisfactory separation of hydrogen chloride from the N-alkyl-2-pyrrolidone.

DESCRIPTION OF THE PREFERRED EMBODIMENTS

This object is achieved by a process for separating hydrogen chloride from a mixture comprising an N-($C_1$–$C_{18}$)-alkyl-2-pyrrolidone and hydrogen chloride, which comprises distilling the mixture comprising an N-($C_1$–$C_{18}$)-alkyl-2-pyrrolidone and hydrogen chloride at from 100 to 220° C. and from 50 to 850 hPa in the presence of water by means of a distillation column, condensing the water as water-hydrogen chloride azeotrope at the top by cooling, returning the water-hydrogen chloride azeotrope to the distillation column, separating off gaseous hydrogen chloride at the top and taking off the N-($C_1$–$C_{18}$)-alkyl-2-pyrrolidone from the bottom.

The process of the invention surprisingly gives both a pure hydrogen chloride which can, for example, be absorbed in water and used further as a water-containing hydrogen chloride and an N-alkyl-2-pyrrolidone which is very largely free of hydrogen chloride and can likewise be reused without additional work-up, for example in the preparation of isochroman-3-ones.

The process of the invention has the advantage that it can be implemented in simple ways without requiring any great engineering outlay.

For the purposes of the present invention, N-alkyl-2-pyrrolidones are compounds of the formula

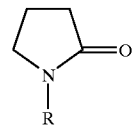

where R is a straight-chain or branched $C_1$–$C_{18}$-alkyl radical.

The N-alkyl-2-pyrrolidones form relatively stable adducts with hydrogen chloride, but these can be dissociated at an elevated temperature (dissociation temperature) into hydrogen chloride and the N-alkyl-2-pyrrolidone. The N-alkyl-2-pyrrolidone-hydrogen chloride adducts tend to form sublimates. This is particularly true of the N-methyl-2-pyrrolidone-HCl adduct, which sublimes relatively easily.

A further advantage of the process of the invention is that the deposition of solids and sublimates which cause blockages in the lines leading from the top of the distillation column is, surprisingly, effectively suppressed.

The mixture comprising the N-alkyl-2-pyrrolidone and HCl can be placed in the bottom of the distillation column and heated (a batchwise procedure). However, it is also possible to feed the mixture comprising the N-alkyl-2-pyrrolidone and HCl in gaseous or liquid form into the distillation column and to carry out the process of the invention continuously. A predetermined amount of water is added to ensure that the distillation proceeds in the presence of water and a water-hydrogen chloride azeotrope can be formed at the top of the distillation column. If the process is carried out continuously, it is advisable to introduce the mixture comprising N-alkyl-2-pyrrolidone and HCl into the lower half, in particular the lower third, of the distillation column and to take off the N-alkyl-2-pyrrolidone which has been very largely freed of HCl at the bottom at a rate corresponding to that at which the mixture is fed into the column.

Pressure and temperature are set so that the mixture comprising hydrogen chloride and the N-alkyl-2-pyrrolidone boils. The process is particularly advantageous when the temperature selected is above the sublimation temperature of the N-alkyl-2-pyrrolidone-HCl adduct. The sublimation temperature of this N-alkyl-2-pyrrolidone-HCl adduct is above the dissociation temperature of the adduct, i.e. above the temperature at which the adduct decomposes into HCl and the N-alkylpyrrolidone.

At the top of the distillation column, a gaseous mixture of water and hydrogen chloride which can still contain small amounts of N-alkyl-2-pyrrolidone is obtained. The water is condensed at the top of the column and is thus obtained as the water-hydrogen chloride azeotrope which may still contain minor amounts of N-alkyl-2-pyrrolidone. At the same time, excess gaseous hydrogen chloride is present at the top of the distillation column. This hydrogen chloride is not condensed together with the water as hydrogen chloride-water azeotrope, but leaves the column at the top as pure hydrogen chloride in gaseous form. Any entrained N-alkyl-2-pyrrolidone or organic product separates out in liquid form. However, the amounts concerned are generally very small.

The water-hydrogen chloride azeotrope condensed at the top by cooling is returned to the distillation column. The water vaporizes again and once more condenses at the top of the distillation column as water-hydrogen chloride azeotrope and is again returned to the distillation column. In this way, the water is circulated.

Since minor amounts of water in the form of water vapor also escape together with the excess gaseous hydrogen chloride which is discharged at the top, it may become necessary to add appropriate amounts of water to the distillation during prolonged operation so as to maintain the formation of the water-hydrogen chloride azeotrope and its return to the distillation to the desired extent.

Should the feed mixture comprising N-alkyl-2-pyrrolidone and hydrogen chloride contain water, it may become necessary during prolonged operation of the distillation, in particular in the case of continuous distillation, to discharge water in the form of the water-hydrogen chloride azeotrope at the top of the column so as to prevent the amount of water from rising in an uncontrolled manner, but instead to limit the proportion of water to the amount required for the distillation.

Good results can be obtained when using a mixture comprising N-($C_1$–$C_{12}$)-alkyl-2-pyrrolidone and hydrogen chloride, in particular N-($C_1$–$C_8$)-alkyl-2-pyrrolidone and hydrogen chloride, preferably N-($C_1$–$C_4$)-alkyl-2-pyrrolidone and hydrogen chloride, particularly preferably N-methyl-2-pyrrolidone and hydrogen chloride.

As mentioned at the outset, the distillation is carried out at a temperature of from 100 to 220° C., in particular from 120 to 200° C., preferably from 130 to 180° C.

The addition of an organic solvent is not necessary, i.e. the distillation is carried out in the absence of an organic solvent.

As mentioned above, the distillation is carried out at a pressure of from 50 to 850 hPa (mbar), in particular from 100 to 400 hPa, preferably from 150 to 350 hPa.

The feed mixture comprising N-alkyl-2-pyrrolidone and hydrogen chloride usually contains from 0.1 to 25% by weight, in particular from 0.7 to 15% by weight, preferably from 1.5 to 10% by weight, of HCl, based on the feed mixture.

A distillation column having an adequate separation performance is employed. In many cases, it is sufficient to use a distillation column having from 2 to 40, in particular from 4 to 30, preferably from 5 to 20, theoretical plates.

The distillation is carried out in the presence of from 0.05 to 15% by weight, in particular from 0.8 to 10% by weight, preferably from 1 to 8% by weight, of water, based on the mixture present in the bottoms and in the distillation column. In many cases, from 2 to 12% by weight, in particular from 3 to 10% by weight, preferably from 3.5 to 8% by weight, of water, based on the mixture present in the bottoms and in the distillation column, have been found to be satisfactory.

A cooler at which the water-hydrogen chloride azeotrope condenses is located at the top of the distillation column. A temperature of from −10 to +60° C., in particular from 0 to 40° C., preferably from 5 to 30° C., is usually set at the top by means of cooling. At these temperatures, which are to a certain extent also dependent on the pressure which has been set and have to be chosen so as to be matched to this pressure, a water-hydrogen chloride azeotrope whose composition depends on the distillation conditions condenses.

Experimental Part

EXAMPLES

Example 1

450 ml of a mixture of N-methyl-2-pyrrolidone (NMP) and HCl (7.2% by weight of HCl) are placed in a heated stirred flask fitted with a small column which is filled with Raschig rings. 10 ml of water are added before heating. At 200 mbar (hPa), reflux is established; the cooling water temperature of the cooler at the top is 10° C. The condensed water-hydrogen chloride azeotrope is returned to the distillation column. The temperature at the bottom is matched to the boiling point of the NMP/HCl mixture. Under the experimental conditions, this is 150° C. The HCl gas formed is obtained in a purity of 99.3% and is absorbed in water in a separate scrubbing column. Samples are regularly taken from the bottom and are titrated against 0.05 mol/l NaOH in order to follow the progress of the HCl removal. The values determined are shown in the following table.

| Time (min) | by weight of HCl |
|---|---|
| 0 | 7.2 |
| 15 | 6.76 |
| 30 | 5.81 |
| 45 | 4.7 |
| 60 | 4.04 |
| 75 | 3.45 |
| 90 | 2.9 |
| 120 | 2.29 |
| 135 | 1.94 |
| 180 | 1.56 |
| 230 | 1.37 |
| 310 | 1.3 |

Comparative Example 1

450 ml of the mixture of N-methylpyrrolidone (NMP) and HCl (7.2% by weight) used in Example 1 are placed in the apparatus employed in Example 1. 10 ml of water are added before heating. At 200 mbar (hPa), reflux is established, but the cooling water temperature of the cooler at the top is set to 70° C. so as to be able to distill off the water. After removal of the water, which is obtained as a water-hydrogen chloride azeotrope, an NMP-HCl adduct begins to condense in the cooler at the top. To avoid blockage of the cooler at the top, the cooling water temperature of the cooler at the top has to be increased to 90° C. The temperature at the bottom is matched to the boiling point of the NMP/HCl mixture. Under the experimental conditions, this is 150° C.

The HCl gas formed is obtained in a purity of only 93.5% and is absorbed in water in a separate scrubbing column. After 330 minutes, the distillation is stopped. The remaining reaction mixture contains 1.33% by weight of HCl.

Example 2

The glass laboratory column used in this experiment is packed with graphite Sulzer packing (BX Type, 1.5 m, diameter 50 mm) and is provided with an 800 ml circulation vaporizer equipped with a quartz heating plug. Before commencement of the experiment, the circulation vaporizer is charged with 800 ml of a mixture of NMP and 5% by weight of HCl and 50 ml of water. The temperature at the bottom is set to 160° C. Total reflux of the water-hydrogen chloride azeotrope is established at 200 mbar. A mixture of NMP and 5% by weight of HCl, which has been preheated to 150° C., is subsequently fed continuously at 200 g/h into the lower third of the column. After 4 hours, a stable temperature profile is established in the column and the N-methylpyrrolidone discharged continuously from the bottom contains only 0.4–0.7% by weight of HCl. The mean residence time of the N-methylpyrrolidone is 4 hours. During the experiment, the temperature at the bottom is 160° C., the cooler temperature is 30° C., the temperature at the top is 68° C. and the pressure is 200 mbar. The HCl gas formed is obtained in a purity of 97.8% and is absorbed as aqueous 30% strength HCl in a downstream scrubbing column.

Example 3

The experiment is carried out in a manner analogous to Example 2, except that the cooler temperature is 10° C. The HCl gas formed is obtained in a purity of 99.4% and is absorbed as aqueous HCl in a downstream scrubbing column.

Example 4

The experiment is carried out in a manner analogous to Example 2, except that the cooler temperature is −10° C. The HCl gas formed is obtained in a purity of 99.8% and is absorbed as aqueous HCl in a downstream scrubbing column.

Comparative Example 2A

The experiment is carried out in a manner analogous to Example 2, except that before commencement of the experiment the circulation vaporizer is charged not with 800 ml of a mixture of NMP and 5% by weight of HCl and 50 ml of water but with 850 ml of a mixture of NMP and 5% by weight of HCl without water. During the experiment, the temperature at the bottom is 160° C., the cooler temperature is 30° C., the temperature at the top is 137° C. and the pressure is 200 mbar. The experiment has to be stopped after about one hour since the deposited solid adduct of N-methylpyrrolidone and hydrogen chloride blocks the cooler.

Comparative Example 2B

The experiment is carried out in a manner analogous to Example 2, except that before commencement of the experiment the circulation vaporizer is charged not with 800 ml of a mixture of NMP and 5% by weight of HCl and 50 ml of water but with 850 ml of a mixture of NMP and 5% by weight of HCl. During the experiment, the temperature at the bottom is 160° C., the cooler temperature is 65° C., the temperature at the top is 137° C. and the pressure is 200 mbar. The cooler temperature is selected so that no solid is deposited. The HCl gas formed is obtained in a purity of 95.5%.

Example 5

200 g/h of a mixture of NMP and 7% by weight of HCl, which has been preheated to 150° C., are fed continuously into the lower third of the column described below. The glass laboratory column used in this experiment is packed with graphite Sulzer packing (BX Type; 1.5 m, diameter: 50 mm) is provided with an 800 ml circulation vaporizer equipped with a quartz heating plug. Before commencement of the experiment, the circulation vaporizer is charged with the mixture of NMP and 7% by weight of HCl and 50 ml of water. Total reflux of the water-HCl azeotrope is established at 200 mbar. The cooler temperature is 10° C. HCl gas formed is continuously removed at the top and is absorbed in water in a downstream scrubbing column. The temperature at the bottom is set to 160° C. The N-methylpyrrolidone discharged from the bottom contains from 0.4 to 0.7% by weight of HCl. The mean residence time of the N-methylpyrrolidone is 4 hours.

What is claimed is:

1. A process for separating hydrogen chloride from a mixture comprising an N-($C_1$–$C_{18}$)-alkyl-2-pyrrolidone and hydrogen chloride, which comprises distilling the mixture comprising an N-($C_1$–$C_{18}$)-alkyl-2-pyrrolidone and hydrogen chloride at from 100 to 220° C. and from 50 to 850 hPa in the presence of water by means of a distillation column, condensing the water as water-hydrogen chloride azeotrope at the top of the column by cooling, returning the water-hydrogen chloride azeotrope to the distillation column, separating off gaseous hydrogen chloride at the top of the column and taking off the N-($C_1$–$C_{18}$)-alkyl-2-pyrrolidone from the bottom of the column.

2. The process as claimed in claim 1, wherein a mixture comprising an N-($C_1$–$C_{12}$)-alkyl-2-pyrrolidone and hydrogen chloride is used.

3. The process as claimed in claim 1, wherein the mixture containing from 0.1 to 25% by weight of hydrogen chloride.

4. The process as claimed in claim 1, wherein the distillation is carried out at from 100 to 400 hPa.

5. The process as claimed in claim 1, wherein the distillation is carried out by means of said distillation column having from 2 to 40 theoretical plates.

6. The process as claimed in claim 1, wherein the distillation is carried out in the presence of from 0.05 to 15% by weight of water, based on the mixture present in the bottom of the distillation column.

7. The process as claimed in claim 1, wherein a temperature of from −10 to +60° C. is set at the top of said distillation column by means of cooling.

* * * * *